(12) United States Patent
Bruder et al.

(10) Patent No.: US 6,262,575 B1
(45) Date of Patent: Jul. 17, 2001

(54) METHOD FOR IMAGING FAT PLAQUE WITH NUCLEAR MAGNETIC RESONANCE TOMOGRAPHY

(75) Inventors: Herbert Bruder, Hoechstadt; Hubertus Fischer, Bamberg, both of (DE)

(73) Assignee: Siemens Aktiengesellschaft, Münich (DE)

( * ) Notice: Subject to any disclaimer, the term of this patent is extended or adjusted under 35 U.S.C. 154(b) by 0 days.

(21) Appl. No.: 09/161,666

(22) Filed: Sep. 29, 1998

(30) Foreign Application Priority Data

Oct. 1, 1997 (DE) ................................ 197 43 547

(51) Int. Cl.$^7$ ............................ G01R 33/20; G01V 3/00
(52) U.S. Cl. ............................ 324/309; 324/307
(58) Field of Search ..................... 324/309, 306, 324/307, 318; 600/410

(56) References Cited

U.S. PATENT DOCUMENTS

| | | |
|---|---|---|
| 4,739,266 | 4/1988 | Kunz . |
| 4,847,559 | 7/1989 | Keren . |
| 5,079,505 | 1/1992 | Deimling et al. . |
| 5,687,725 | 11/1997 | Wendt . |
| 5,821,751 | 10/1998 | Wendt et al. . |
| 6,005,391 | * 12/1999 | Bonert et al. ............... 324/309 |

FOREIGN PATENT DOCUMENTS 0 571 071  3/1993 (EP) .

OTHER PUBLICATIONS

"Simple Proton Spectroscopic Imaging," Dixon, Radiology, vol. 153 (1984), pp. 189–194.
"Echo–Planar Spin–Echo and Inversion Pulses," Pauly et al., MRM vol. 29 (1993), pp. 776–782.
"Wavelet–Encoded MR Imaging," Weaver et al., Magnetic Resonance in Medicine, vol. 24 (1992), pp. 275–287.
"Multi–planar Image Formation Using NMR Spin Echoes," Mansfield, Journal of Physics C, vol. 10 (1997).

* cited by examiner

*Primary Examiner*—Christine Oda
*Assistant Examiner*—Tiffany A. Fetzner
(74) *Attorney, Agent, or Firm*—Schiff Hardin & Waite

(57) ABSTRACT

In a method for producing an image of fat plaque employing nuclear magnetic resonance tomography, a radio-frequency excitation pulse is emitted with wavelet coding in the presence of a first gradient, refocusing pulses are emitted which are selective to the spectral frequency of fat, and the resulting nuclear magnetic resonance signals are read out in the presence of a further magnetic field gradient. An image of fat plaque with enhanced spatial resolution is thereby produced.

8 Claims, 2 Drawing Sheets

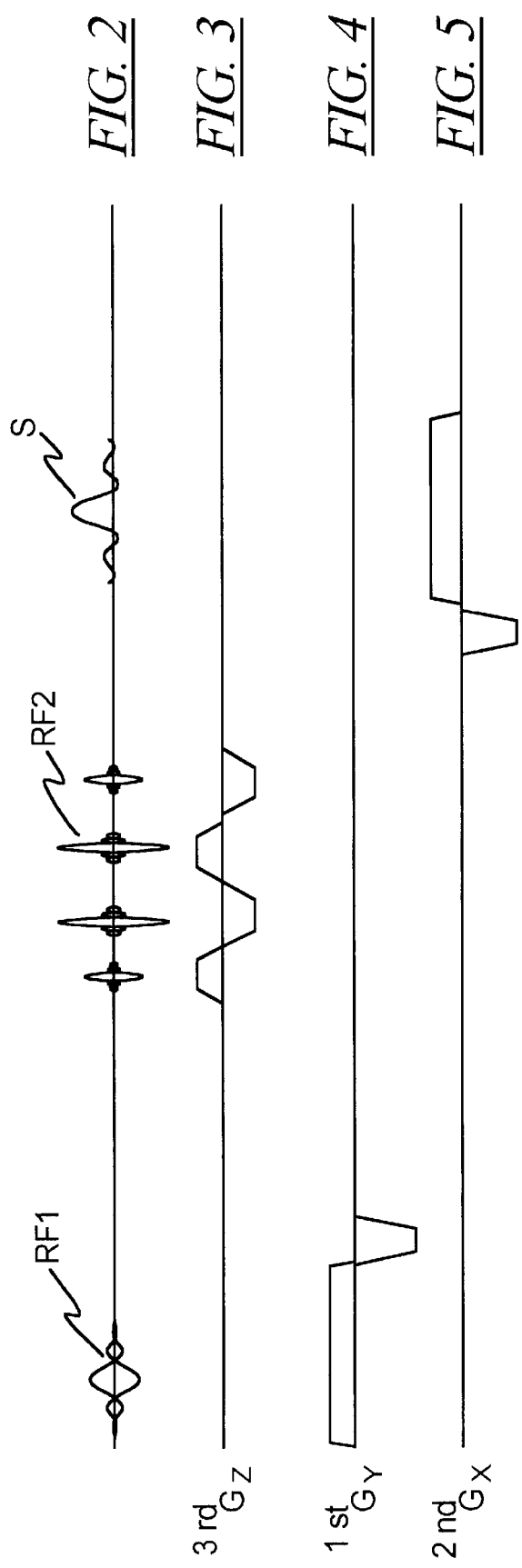

ND FOR IMAGING FAT PLAQUE
METHOD FOR IMAGING FAT PLAQUE WITH NUCLEAR MAGNETIC RESONANCE TOMOGRAPHY

BACKGROUND OF THE INVENTION

1. Field of the Invention

The present invention is directed to a method employing nuclear magnetic resonance tomography for producing an image of fat plaque in an examination subject.

2. Description of the Prior Art

The presentation of calcification by computed tomography is usually employed as a non-invasive modality for diagnosing a constriction or a closure of arteries. This type of diagnosis is particularly important with respect to coronary arteries since a cardiac infarction can result from the constriction. The presentation of the calcification, however, is a relatively unreliable criterion for identifying the presence of constriction. First, the deposit of calcium need not necessarily indicate a constriction; second, a constriction can be present before a deposit of calcium occurs. The method hitherto applied is therefore unsatisfactory with respect to the sensitivity as well as with respect to the specificity.

The deposit of lipids (fats) in the vessels is considered a more reliable indicator for a constriction or a closure of arteries. Nuclear magnetic resonance tomography fundamentally allows fat deposits to be non-invasively displayed. A problem, however, is to display an adequate spatial resolution. Large coronary vessels have a diameter of approximately 3 through 5 mm. The fat plaque occupies 10 through 20% of the vessel diameter in an early phase and can amount to 70% later. An illustration of fat plaque in the coronary arteries and an evaluation of the degree of stenosis therefore presumes a spatial resolution in the sub-millimeter range. The spatial resolution also is degraded by the movement of the heart.

The presentation of coronary arteries in a MR image is known in general. In order to keep the measuring time optimally short, for example, the especially fast EPI (Echo Planar Imaging) technique is applied as proposed, among others, in the reference P. Mansfield, "Multiplanar Image Formation Using NMR Spin Echos", Journal of Physics C, 10 (1977). Since the originally proposed "single shot" EPI method wherein the k-space is sampled after one excitation makes extreme demands on the magnetic field gradients, a segmented EPI method is also often employed. After an excitation, only a part of the k-space is sampled, i.e. the entire measurement for the data of a tomogram comprises a number of excitations.

Methods are also known wherein essentially only fat is portrayed in the acquired image. These methods can be classified into methods having spectrally-selective excitation or saturation, and phase-difference methods. For example, the article by J. Pauly et al., Echo Planar Spin Echo and Inversion Pulses, MRM 29, pages 776–782 (1993), presents a possibility of designing excitation pulses which, under the influence of a gradient, are both spatially selective (i.e., for example, excite only one slice of an examination subject) and spectrally selective, so that, for example, only fat protons are excited. In the saturation method, the water protons are saturated in a preparation phase and the fat protons are subsequently excited, so that only the latter have a signal-producing effect.

The phase-difference method known, for example, from W. Thomas Dixon, Simple Proton Spectroscopic Imaging, Radiology 1984, 153, pages 189–194, makes use of the fact that the Larmor frequencies of fat and water protons are somewhat different, and thus the phase of the corresponding transverse magnetization diverges. By forming the difference at suitable points in time, the fat signal can be separated from the water signal.

The FFT (Fast Fourier Transform) method applied in a standard way in nuclear magnetic resonance tomography has the property that the entire field of view (FOV) is acquired with constant resolution per direction. U.S. Pat. No. 5,687,725 discloses a method wherein wavelet coding is used as an alternative to the FFT method. Individual image regions within an observation window can thereby be presented with higher resolution.

None of these methods supplies a satisfactory presentation of fat plaque.

SUMMARY OF THE INVENTION

It is therefore an object of the invention to provide a method for the presentation of fat plaque with nuclear magnetic resonance tomography that satisfies diagnostic requirements.

The above object Is achieved In accordance with the principles of the present invention in a method for producing an image of fat plaque using nuclear magnetic resonance tomography, wherein a radio-frequency excitation pulse is emitted with wavelet coding in the presence of a first magnetic field gradient, refocusing pulses are emitted which are selective to the spectral frequency of fat, and the resulting nuclear magnetic resonance signal is read out in the presence of a further magnetic field gradient.

In the inventive method a fat image is obtained wherein an adequate resolution can be achieved on the basis of wavelet coding in the region of the arteries to be portrayed, so that fat plaque can be well-presented.

The direction of enhanced resolution can be oriented by wavelet coding in a direction perpendicular to a vessel wall so that the evaluation of the degree of stenosis is enabled.

The aforementioned inventive method can be embodied in an overall examination procedure wherein an overview or planning exposure is first obtained, and a fat image is produced with "normal" resolution. Locations which are likely to contain fat plaque are then identified from the normal resolution image, and a fat image with enhanced resolution is then produced in the identified regions, in accordance with the above-described inventive method.

DESCRIPTION OF THE DRAWINGS

FIGS. 2–5 collectively illustrate signals which are generated in a nuclear magnetic resonance tomography apparatus during execution of the inventive method, in the form of a pulse sequence.

DESCRIPTION OF THE PREFERRED EMBODIMENTS

Figure 1:
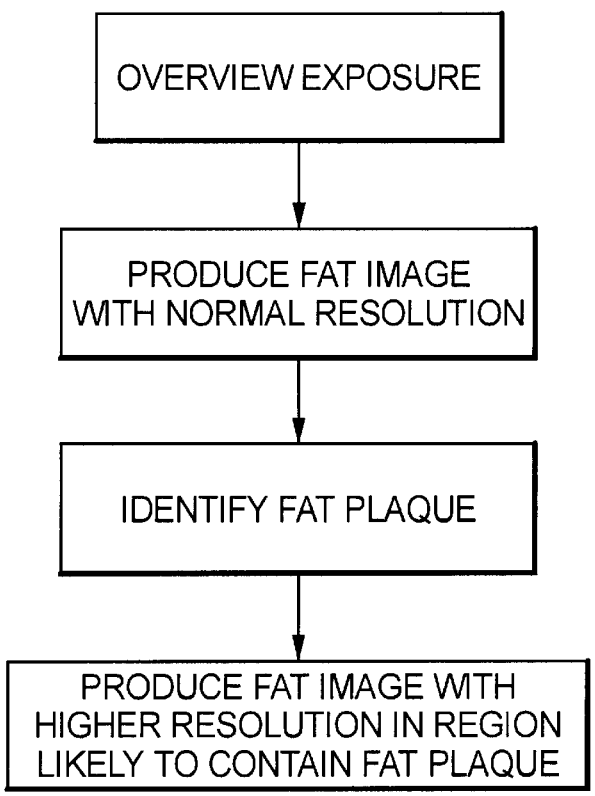
FIG. 1 is a flow chart showing an overall examination procedure incorporating the production of a fat image with enhanced resolution in accordance with the principles of the inventive method.

According to the flowchart of FIG. 1, an overview exposure of the heart is first produced in the form of a conventional MR image. With the assistance of this overview image, only the arteries to be examined, for example the coronary arteries, are spatially identified. Fundamentally, any conventional pulse sequence is suitable for this overview image. The EPI sequence already mentioned has the advantage that it is especially fast.

In the second step, a fat image is produced with "normal" resolution. As used herein normal resolution is typically a spatial resolution of 1–2 mm. Fat plaque which may be present in the arteries can be identified at this resolution, but a reliable evaluation of the degree of stenosis, and thus the threat of a vessel constriction is not yet possible. Fundamentally all methods for the acquisition of fat images cited in the introduction to the specification are suitable for this step, i.e. both methods with frequency-selective excitation or, respectively, saturation as well as phase-difference methods. These first and second steps can ensue in one measurement wherein the MR signals for fat and water image are simultaneously acquired.

The fat plaque identified in the second step is presented with enhanced resolution in a third step. A new method that is based on wavelet coding is applied for this purpose. FIGS. 2 through 5 show an exemplary embodiment of a corresponding pulse sequence.

FIGS. 2 through 5 show a pulse sequence for the third step of the method i.e. for the acquisition of a fat image with enhanced topical resolution. A wavelet coding as was already fundamentally described in an article by J. Weaver et al., Magnetic Resonance in Medicine 24, 275–287 (1992) is thereby applied in one direction. The application of a wavelet coding was disclosed in U.S. Pat. No. 5,687,725, but for motion tracking of interventional instruments. The aforementioned publications are referenced with respect to the fundamentals of wavelet coding.

Given the exemplary pulse sequence according to FIGS. 2 through 5, a radio-frequency pulse RF1 is first emitted under the influence of a gradient $G_y$. In combination with the gradient $G_y$, the frequency spectrum of the radio-frequency pulse RF1 determines dilatation and translation of the wavelet function. A stripe profile perpendicular to the direction of the gradient $G_y$ can thereby be intentionally selected, whereby this stripe profile is placed such that it contains the vessel to be observed in greater detail. An enhanced resolution is achieved in the y-direction within the stripe profile. The envelope of this radio-frequency pulse RF1 and the stripe profile required here are a Fourier transform pair for small flip angles of the radio-frequency pulse RF1. The dilatation a and the intensity of the gradient $G_y$ behave proportionally relative to one another. Given an intensification of the gradient Gy, a is therefore enlarged and the stripe width is therefore reduced. The required translation b can be achieved by shifting the center frequency of the radio-frequency pulse RF1 or by an offset of the gradient $G_y$. Subsequently, the gradient $G_y$ is inverted in order to cancel the dephasing caused by the positive sub-pulse.

Although a spatial encoding of the excited signals is obtained with this type of excitation, the excitation is not spectrally selective with respect to fat and water, i.e. protons in fat as well as in water are excited. The spectral sensitivity is obtained by subsequent inversion pulses RF2 in combination with a gradient $G_z$ of alternating polarity. Such a pulse sequence—as explained in the aforementioned article by J. Pauly et al.—can be fashioned such that a spin inversion selectively ensues spectrally as well as spatially. In the present case, only the fat protons are refocused in a slice lying perpendicular to the gradient $G_z$, so that a nuclear magnetic resonance signal S is obtained only from these protons in a following readout phase. This signal is readout under the influence of a readout gradient $G_x$ and is thus frequency-coded in the x-direction.

With the described pulse sequence, a nuclear magnetic resonance signal of the fat protons thus is obtained that has a wavelet coding with respect to the y-direction and a frequency coding with respect to the x-direction. A slice selection is present in the y-direction. Using known reconstruction methods, a fat image can be obtained from a number of such signals that exhibits an enhanced resolution in the y-direction because of the above-described, advantageous properties of the wavelet coding within a stripe profile selected in the wavelet coding. Since this stripe profile is placed such that it covers the vessel to be observed, the desired fat image for the vessel is acquired with enhanced spatial resolution.

Figure 6:
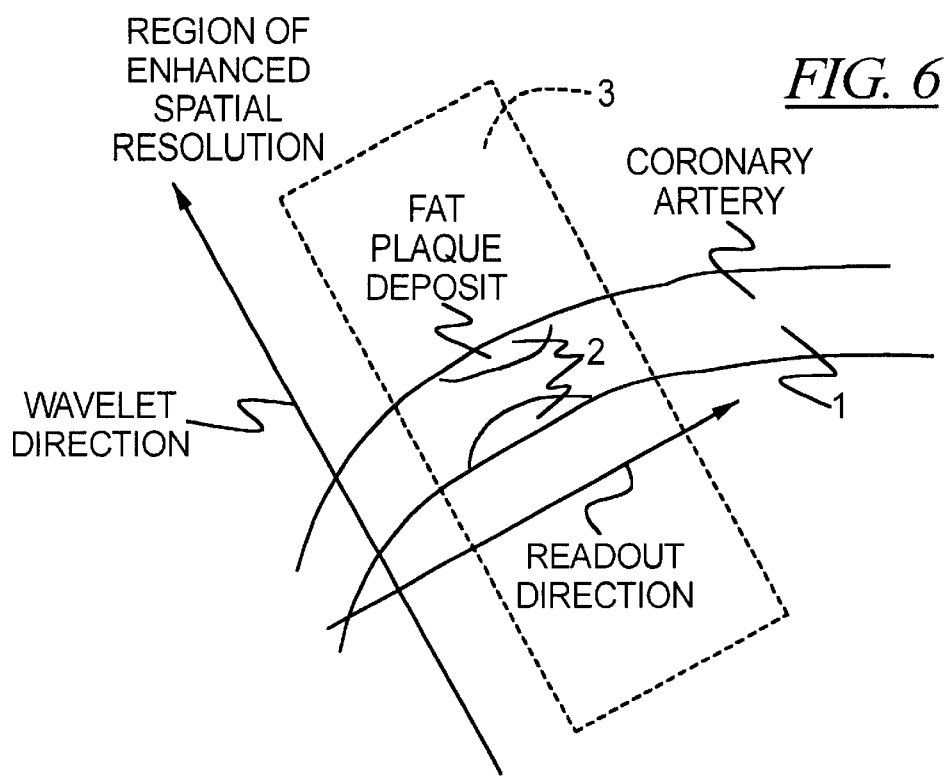
FIG. 6 illustrates selection of the wavelet coding direction relative to an artery containing fat plaque, in accordance with the inventive method.

For illustration, a coronary artery 1 with fat plaque deposit 2 is shown in FIG. 6. The vessel constriction by the fat plaque must be identified for evaluating the degree of stenosis. It is thus particularly the resolution in a direction perpendicular to the coronary artery 1 that is of significance. The wavelet coding is therefore implemented perpendicularly to the coronary artery 1, whereas the spatial resolution ensues in the artery direction by frequency coding during the readout phase. The selected slice lies parallel to the coronary artery 1. Transferred to the pulse sequence according to FIGS. 2 through 5, this means that the x-direction, i.e. the direction of the gradient $G_x$, lies in the direction of the coronary artery 1 and the y-direction and the z-direction are perpendicular thereto. The region of enhanced spatial resolution is designated 3 in FIG. 6.

In order to enable an exact spatial allocation of the fat plaque identified with enhanced spatial resolution with the wavelet coding relative to the anatomy of the patient, the conventional image according to the first step, the fat image according to the second step and the fat image with enhanced spatial resolution according to the third step can be superimposed with precise spatial allocation.

A poorer signal-to-noise ratio is unavoidable with wavelet coding compared to that with conventional phase coding. As needed, however, a number of signals can be averaged in order to achieve an adequate signal-to-noise ratio. The overall image acquisition can generally not ensue within one heartbeat. Typically, therefore, the image acquisition will be made over a number of heartbeats and the data acquisition will be triggered with the heartbeat, for example derived from the ECG. One measurement or a series of measurements are respectively triggered in the same phase of a heart cycle. Another possibility would be to "gate" the data acquisition, i.e. to evaluate the respective data that were acquired in the same heart phase a continuously proceeding pulse sequence. The motion due to respiration can, for example, be largely eliminated by placing the patient in a prone position, however, an additional synchronization of the measurement with respiratory motion is also possible.

Although modifications and changes may be suggested by those skilled in the art, it is the intention of the inventor to embody within the patent warranted hereon all changes and modifications as reasonably and properly come within the scope of his contribution to the art.

We claim as our invention:

1. A method for producing an image of fat plaque using nuclear magnetic resonance tomography, comprising the steps of:

(a) emitting a radio-frequency excitation pulse into a subject containing fat plaque, with wavelet coding in the presence of a first magnetic field gradient;

(b) emitting a plurality of refocusing pulses and a second magnetic field gradient with alternating polarity so that only fat protons are refocused; and (c) reading out nuclear magnetic resonance signals from said subject in the presence of a third magnetic field gradient.

2. A method as claimed in claim 1 wherein said plaque is disposed in said examination subject within a blood vessel wall, and wherein step (b) comprises implementing said wavelet coding in a direction perpendicular to said vessel wall.

3. A method as claimed in claim 1 comprising the additional steps of producing a conventional nuclear magnetic resonance tomography overview image of said subject;

identifying at least one region in said overview image for detailed examination;

producing a fat image to identify fat-plaque within said region; and conducting steps (a), (b) and (c) only in respective portions of said region identified as containing fat.

4. A method as claimed in claim 3 wherein said fat plaque is disposed in said examination subject in proximity to a heart, and comprising the additional step of triggering said overview image and an image obtained from steps (a), (b) and (c) by a heartbeat of said heart.

5. A method as claimed in claim 3 wherein said fat plaque is disposed in said examination subject in proximity to a heart, and comprising the additional step of gating said overview image and an image obtained from steps (a), (b) and (c) by a heartbeat of said heart.

6. A method as claimed in claim 3 wherein the step of acquiring a fat image comprises employing a phase-difference method for acquiring said fat image.

7. A method as claimed in claim 3 comprising the additional step of saturating a spectral component of water in said subject prior to acquisition of said fat image.

8. A method as claimed in claim 3 wherein the step of acquiring said fat image includes selectively exciting nuclear spins in said subject at said spectral frequency of fat.

* * * * *